United States Patent [19]

Peglion et al.

[11] Patent Number: 5,780,474

[45] Date of Patent: Jul. 14, 1998

[54] 3-(PIPERID-4-YL)-1,2-BENZISOXAZOLE AND 3-(PIPERAZIN-4-YL)-1,2-BENZISOXAZOLE COMPOUNDS

[75] Inventors: Jean-Louis Peglion, Le Vesinet; Mark Millan, Le Pecq; Mauricette Brocco, Paris; Valérie Audinot, Poissy, all of France

[73] Assignee: Adir et Compagnie, Courbevoie, France

[21] Appl. No.: 868,116

[22] Filed: Jun. 3, 1997

[30] Foreign Application Priority Data

Jun. 4, 1996 [FR] France .................... 96 06866

[51] Int. Cl.$^6$ .................... A61K 31/495; A61K 31/44; C07D 413/14
[52] U.S. Cl. .................... 514/254; 514/321; 544/295; 544/316; 544/368; 546/198
[58] Field of Search .................... 544/368, 295, 544/316; 546/198; 514/254, 321

[56] References Cited

U.S. PATENT DOCUMENTS 4,352,811  10/1982  Strupczewski et al. ............ 546/198
4,458,076   7/1984  Strupczewski .................... 546/198
5,599,815   2/1997  Fukuda et al. .................... 514/254
5,599,821   2/1997  Glamkowski et al. ............. 514/321

*Primary Examiner*—Emily Bernhardt
*Attorney, Agent, or Firm*—The Firm of Gordon W. Hueschen

[57] ABSTRACT

Compounds of formula:

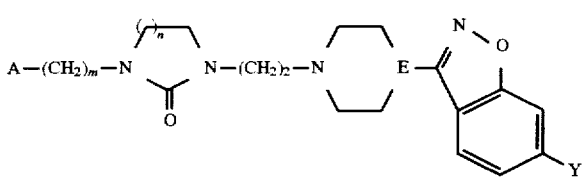

wherein:

A, m, n, E and Y are as defined in the description, the optical isomers thereof and the physiologically-tolerable salts thereof.

These compounds, their optical isomers and their physiologically-tolerable salts, can be used as medicaments in the treatment of psychotic disorders, anxio-depressive disorders, and aggressiveness.

6 Claims, No Drawings

3-(PIPERID-4-YL)-1,2-BENZISOXAZOLE AND 3-(PIPERAZIN-4-YL)-1,2-BENZISOXAZOLE COMPOUNDS

The present invention relates to new 1,2-benzisoxazole compounds and to pharmaceutical compositions containing them.

Many 3-(piperid-4-yl)-1,2-benzisoxazole and 3-(piperazin-4-yl)-1,2-benzisoxazole compounds are known in the literature. Patent specifications WO 9418197, US 4,458,076A and US 4,352,811A describe compounds which most closely resemble the compounds of the present Application. Those compounds have anti-psychotic or analgesic properties.

The compounds of the present invention are 3-(piperid-4-yl)-1,2-benzisoxazole and 3-(piperazin-4-yl)-1,2-benzisoxazole compounds which are distinguished from the known compounds by their substituent in the 1-position of the piperidine or piperazine ring and by their pharmacological properties. In fact, various pharmacological tests carried out, both in vitro and in vivo, have shown that the compounds of the invention are antagonists of $5HT_{2A}$ serotonin receptors, $\alpha_1$-adrenergic receptors and of dopaminergic receptors. They have an anti-psychotic activity that is comparable to that of the reference products, such as haloperidol and risperidone, but especially they do not induce side-effects, especially extrapyramidal effects. It is known that anti-psychotics often cause very significant side-effects, which limits their use. The extrapyramidal side-effects are clearly related to the $D_2$ dopaminergic receptor blocking properties of the anti-psychotic compounds in clinical use. The compounds of the present invention are much weaker $D_2$ dopaminergic blockers than the known products. On the other hand, their affinity for the $D_4$ dopaminergic receptors is very high and is clearly greater than their affinity for the $D_2$ receptor. That selectivity thus explains the absence of side-effects of the extrapyramidal type shown by the products of the present invention.

The hyperactivity of the dopaminergic system is implicated not only in schizophrenia but in a large number of disorders of the central nervous system, such as anxiety or depressive disorders, impulsive disorders and aggressiveness. The products of the invention are thus more especially used as anti-psychotics, anxiolytics and anti-aggressives. They can also be used as antalgics.

The present invention relates especially to the 1,2-benzisoxazole compounds of formula I

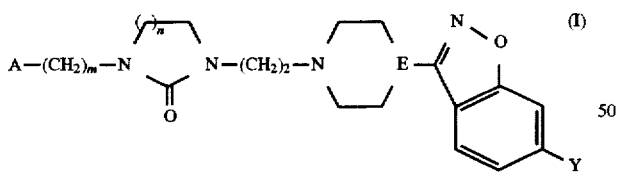

wherein:
A is selected from the group consisting of linear and branched alkyl having from 1 to 10 carbon atoms inclusive, unsubstituted phenyl, halophenyl, hydroxyphenyl and (lower alkoxy)phenyl,
m is selected from zero and 1,
n is selected from 1 and 2,
E is selected from the group consisting of N and CH, and
Y is selected from the group consisting of hydrogen, halogen, and alkoxy having from 1 to 5 carbon atoms inclusive, and also the optical isomers thereof, where they exist, and the addition salts thereof with pharmaceutically acceptable organic and mineral acids.

The compounds of formula I are prepared by a process characterised in that:
a compound of formula II

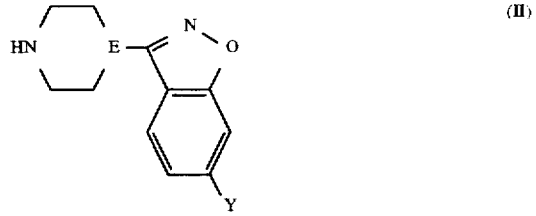

wherein E and Y are as defined hereinbefore, is reacted either with a compound of formula III

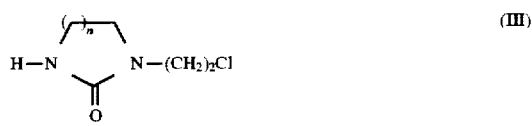

wherein n is as defined hereinbefore, in the presence of an alkali metal carbonate, such as, for example, potassium carbonate, in a polar solvent, such as, for example, methyl ethyl ketone or methyl isobutyl ketone, to obtain a compound of formula IV

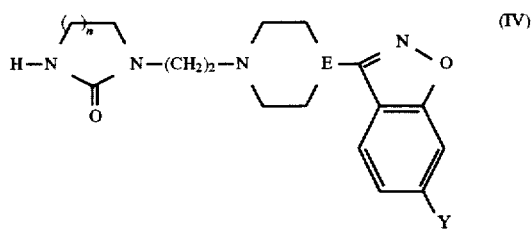

wherein n, E and Y are as defined hereinbefore, which is then reacted with a compound of formula V

wherein A and m are as defined hereinbefore and X is a halogen atom, in the presence of an alkali metal hydride, such as, for example, sodium hydride, in a polar solvent, such as, for example, dimethyl sulphoxide, to obtain the compounds of formula I; or
with a compound of formula VI

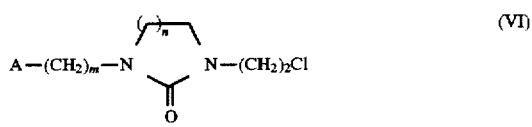

wherein A, m and n are as defined hereinbefore, in the presence of an alkali metal carbonate, such as potassium carbonate, in a polar solvent, such as acetone or methyl isobutyl ketone, to form the compounds of formula I.

Compounds III and VI are known products or are prepared from known starting materials in accordance with conventional methods of synthesis.

The compounds of the present invention differ from the compounds of the prior art not only in their chemical structure but also in respect of their pharmacological and therapeutic activities. Those activities have been demonstrated:

In vitro by cloned human $D_2$ and $D_4$ receptor-, $5HT_{2A}$ receptor- and $\alpha_1$ receptor-binding studies.

In vivo
in the model of verticalisation induced by apomorphine in the mouse,
in the model of active avoidance conditioning in the rat, and
in the model of aggressiveness in isolated mice.

Finally, it has also been possible to verify the absence of side-effects in the model of catalepsy in the rat.

Those activities and the absence of troublesome side-effects render the compounds of the present invention especially valuable for use as medicaments in the treatment of psychotic disorders, anxiety or depressive disorders and aggressiveness.

The present invention relates also to pharmaceutical compositions comprising as active ingredient a compound of formula I or a physiologically tolerable salt thereof, in mixture or association with one or more pharmaceutically appropriate excipients.

The pharmaceutical compositions so obtained are generally in unit dose form containing from 0.5 to 25 mg of active ingredient. They may, for example, be in the form of tablets, dragees, gelatin capsules, suppositories or injectable or drinkable solutions, and may be administered by the oral, rectal or parenteral route.

The dosage may vary according to the age and weight of the patient, the route of administration, the nature of the disorder and associated treatments, and ranges from 0.5 to 25 mg of active ingredient, from 1 to 3 times per day.

The following Examples, given by way of non-limiting example, illustrate the present invention. The melting points were determined using a Kofler hot plate under a microscope.

EXAMPLE 1

1-{2-[4-(6-Fluoro-1,2-benzisoxazol-3-yl)piperid-1-yl]ethyl}-3-isopropylimidazolidin-2-one Step 1

1-{2-[4-(6-Fluoro-1,2-benzisoxazol-3-yl)piperid-1-yl] ethyl}imidazolidin-2-one 21.4 g (0.144 mol) of 1-(2-chloroethyl)imidazolidin-2-one, 23.6 g (0.107 mol) of 4-(6-fluoro-1,2-benzisoxazol-3-yl)piperidine, 92.9 g (0.67 mol) of potassium carbonate, 2.6 g of potassium iodide and 524 ml of methyl isobutyl ketone are placed in a three-necked flask. Refluxing is carried out for one night, and then the reaction mixture is concentrated and taken up in a mixture of water/ethyl acetate. Decanting is carried out, and the organic phase is washed several times with water and then extracted with a normal solution of hydrochloric acid. The acidic phase is then rendered basic with sodium hydroxide solution and extracted with methylene chloride. Drying is carried out over $MgSO_4$. After evaporation, the residue is recrystallised from 80 ml of acetonitrile to yield 22 g of a solid that corresponds to the expected product. M.p.=137°–141° C. (Yield=46%).

Step 2

Title compound 5 g (0.015 mol) of the product obtained in the preceding Step are dissolved in 16 ml of dimethyl sulphoxide. 1.2 g (0.03 mol) of 60% sodium hydride are added in portions. The reactants are left in contact for half an hour, and then 4.22 ml (0.045 mol) of 2-bromopropane are poured in. The mixture is stirred at room temperature overnight. The mixture is taken up in $H_2O$, and then in methylene chloride. Decanting is carried out, and the organic phase is washed with brine, dried over $MgSO_4$ and concentrated in vacuo. The oil obtained is chromatographed on silica (eluant: $CH_2Cl_2/CH_3OH$ 95:5) to yield the expected product. M.p.= 121°–123° C. (Yield=39%).

EXAMPLE 2

1-{2-[4-(6-Fluoro-1,2-benzisoxazol-3-yl)piperazin-1-yl]ethyl}-3-isopropylimidazolidin-2-one This product is prepared in the same manner as the compound of Example 1 but using 4-(6-fluoro-1,2-benzisoxazol-3-yl)piperazine instead of 4-(6-fluoro-1,2-benzisoxazol-3-yl)piperidine in Step 1. The title compound so obtained melts at 125°–127° C.

EXAMPLE 3

1-{2-[4-(6-Fluoro-1,2-benzisoxazol-3-yl)piperazin-1-yl]ethyl}-3-ethylimidazolidin-2-one This product is prepared in the same manner as the compound of Example 1 but using 4-(6-fluoro-1,2-benzisoxazol-3-yl)piperazine instead of 4-(6-fluoro-1,2-benzisoxazol-3-yl)-piperidine in Step 1, and using bromoethane instead of 2-bromopropane in Step 2. The hydrochloride of the title compound so obtained melts at 201°–204° C.

EXAMPLE 4

1-{2-[4-(6-Fluoro-1,2-benzisoxazol-3-yl)piperid-1-yl]ethyl}-3-isobutylimidazolidin-2-one This product is prepared in the same manner as the compound of Example 1 but using 1-bromo-2-methylpropane instead of 2-bromopropane in Step 2.

EXAMPLE 5

1-{2-[4-(6-Fluoro-1,2-benzisoxazol-3-yl)piperid-1-yl]ethyl}-3-phenylimidazolidin-2-one Step 1

1,1-[Di-(2-hydroxyethyl)]-3-phenylurea

A mixture of 15.62 ml (0.136 mol) of diethanolamine and 163 ml of methylene chloride is poured, at a temperature of 10° C., into a three-necked flask containing 18.25 ml (0.168 mol) of phenyl isocyanate dissolved in 37 ml of $CH_2Cl_2$. The mixture is left at that temperature for one hour, and then at room temperature overnight, and concentrated in vacuo to obtain 36.5 g of the expected product. (Yield=100%).

Step 2

1,1-[Di-(2-chloroethyl)]-3-phenylurea 39 g (0.137 mol) of the product obtained in the preceding Step are dissolved in 100 ml of methylene chloride. Maintaining the temperature at 0° C., 26.64 ml (0.365 mol) of thionyl chloride are poured in. The mixture is refluxed for 4 hours and left at room temperature overnight, and concentrated in vacuo to obtain 43.7 g of the expected product. (Yield=96%).

Step 3

1-(2-Chloroethyl)-3-phenylimidazolidin-2-one 43.7 g (0.167 mol) of the product obtained in Step 2 are heated at 120° C. for 3 hours, then at 140° C. for 6 hours. Once the evolution of gas has ceased and after cooling, the oil obtained is chromatographed on silica (eluant: methylene chloride 100%) to yield 23.2 g of a white solid that corresponds to the expected product. M.p.=92° C. (Yield=61.7%).

Step 4

Title compound

The same procedure is used as that described in Step 1 of Example 1 but with replacement of the 1-(2-chloroethyl) imidazolidin-2-one by 1-(2-chloroethyl)-3-phenylimidazolidin-2-one. Purification by chromatography on silica (eluant: CH$_2$Cl$_2$/cyclohexane 80:20) yields 3.8 g of the expected product. M.p.=158°–160° C. (Yield=56%).

EXAMPLE 6

1-{2-[4-(6-Fluoro-1,2-benzisoxazol-3-yl)piperid-1-yl]ethyl}-3-tert-butylimidazolidin-2-one This product is obtained in the same manner as the compound of Example 5, but with replacement of the phenyl isocyanate by tert-butyl isocyanate in Step 1 of the synthesis. The hydrochloride of the title compound melts at 205°–208° C.

EXAMPLE 7

3-Benzyl-1-{2-[4-(6-fluoro-1,2-benzisoxazol-3-yl)piperid-1-yl]ethyl}imidazolidin-2-one This product is obtained in the same manner as the compound of Example 5, but with replacement of the phenyl isocyanate by benzyl isocyanate in Step 1 of the synthesis. The expected product melts at 126°–130° C.

EXAMPLE 8

1-{2-[4-(6-Fluoro-1,2-benzisoxazol-3-yl)piperid-1-yl]ethyl}-3-(2-ethoxyphenyl)imidazolidin-2-one This product is obtained in the same manner as the compound of Example 5, but with replacement of the phenyl isocyanate by 2-ethoxyphenyl isocyanate in Step 1 of the synthesis. The hydrochloride of the title compound melts at 214°–218° C.

EXAMPLE 9

1-{2-[4-(6-Fluoro-1,2-benzisoxazol-3-yl)piperid-1-yl]ethyl}-3-(2-chlorophenyl)imidazolidin-2-one This product is obtained in the same manner as the compound of Example 5, but with replacement of the phenyl isocyanate by 2-chlorophenyl isocyanate in Step 1 of the synthesis. The hydrochloride of the title compound melts at 223°–227° C.

EXAMPLE 10

1-{2-[4-(6-Fluoro-1,2-benzisoxazol-3-yl)piperid-1-yl]ethyl}-3-(3-chlorophenyl)imidazolidin-2-one This product is obtained in the same manner as the compound of Example 5, but with replacement of the phenyl isocyanate by 3-chlorophenyl isocyanate in Step 1 of the synthesis. The hydrochloride of the title compound melts at 223°–227° C.

EXAMPLE 11

1-{2-[4-(6-Fluoro-1,2-benzisoxazol-3-yl)piperid-1-yl]ethyl}-3-(2,6-dichlorophenyl)imidazolidin-2-one This product is obtained in the same manner as the compound of Example 5, but with replacement of the phenyl isocyanate by 2,6-dichlorophenyl isocyanate in Step 1 of the synthesis. The hydrochloride of the title compound melts at 237°–241° C.

EXAMPLE 12

1-{2-[4-(6-Fluoro-1,2-benzisoxazol-3-yl)piperid-1-yl]ethyl}-3-(4-methoxyphenyl)imidazolidin-2-one This product is obtained in the same manner as the compound of Example 5, but with replacement of the phenyl isocyanate by 4-methoxyphenyl isocyanate in Step 1 of the synthesis. The expected product melts at 154°–157° C.

EXAMPLE 13

1-{2-[4-(6-Fluoro-1,2-benzisoxazol-3-yl)piperid-1-yl]ethyl}-3-(2,3-dichlorophenyl)imidazolidin-2-one This product is obtained in the same manner as the compound of Example 5, but with replacement of the phenyl isocyanate by 2,3-dichlorophenyl isocyanate in Step 1 of the synthesis. The hydrochloride of the title compound melts at 218°–222° C.

EXAMPLE 14

1-{2-[4-(6-Fluoro-1,2-benzisoxazol-3-yl)piperid-1-yl]ethyl}-3-(4-hydroxyphenyl)imidazolidin-2-one This product is obtained in the same manner as the compound of Example 5, but with replacement of the phenyl isocyanate by 4-hydroxyphenyl isocyanate in Step 1 of the synthesis. The expected product melts at 190°–194° C.

EXAMPLE 15

1-{2-[4-(6-Fluoro-1,2-benzisoxazol-3-yl)piperid-1-yl]ethyl}-3-phenyl-3,4,5,6-tetrahydro-(2H)-pyrimidin-2-one Step 1

1-Phenyl-3,4,5,6-tetrahydro-(2H)-pyrimidin-2-one 2.5 g (16.5 mM) of N$^1$-phenylpropane-1,3-diamine are dissolved in 56.5 ml of anhydrous tetrahydrofuran. A mixture of 3.8 g (23.3 mM) of carbonyldiimidazole in 115 ml of anhydrous tetrahydrofuran is poured into the solution, and the mixture is left at room temperature overnight. The mixture is concentrated, taken up in ethyl acetate, washed with normal HCl and dried over MgSO$_4$ to yield 2 g of a white solid that melts at 210°–211° C. and corresponds to the expected product.

Step 2

1-(2-Chloroethyl)-3-phenyl-3,4,5,6-tetrahydro-(2H)-pyrimidin-2-one 1.76 g (10 mM) of the product obtained in the preceding Step are dissolved in 15 ml of anhydrous dimethyl sulphoxide. 0.81 g (20 mM) of 60% NaH is added in portions. The reactants are left in contact for 2 hours, and then 1.7 ml (20 mM) of 1-bromo-2-chloroethane are poured in. The mixture is left at room temperature over a weekend. 350 ml of distilled water are added and then extraction is carried out with methylene chloride. Decanting is carried out, and the organic phase is washed and dried over MgSO$_4$. Evaporation yields 1.8 g of an oil that corresponds in structure to the expected product. (Yield=76%).

Step 3

Title compound

The same procedure is used as that described in Step 1 of Example 1, but with replacement of the 1-(2-chloroethyl) imidazolidin-2-one by the 1-(2-chloroethyl)-3-phenyl-3,4,5,6-tetrahydro-(2H)-pyrimidin-2-one obtained above. Purification by chromatography on silica (eluant: CH$_2$Cl$_2$/cyclohexane 80:20) yields the expected product.

EXAMPLE 16

Pharmacological study

In vitro

The interaction of the compounds with the 5HT$_{2A}$ serotoninergic, $\alpha_1$-adrenergic and D$_2$ and D$_4$ dopaminergic receptors was determined using conventional binding studies, according to Millan et al (J. Pharm. Exp. Ther., 275, 885–898, 1995). The conditions are detailed below:

| Receptor | Species, tissue | [³H]-ligand (nM) | NSB (10 μM) | Duration of incubation, T° |
|---|---|---|---|---|
| 5HT$_{2A}$ | rat, frontal cortex | ketanserin (1.0) | spiperone | 90 min, 25° C. |
| α$_1$ | rat, frontal cortex | prazosin (0.2) | phentolamine | 60 min, 25° C. |
| D$_2$ | rat, striatum | spiperone (0.2) | raclopride | 30 min, 37° C. |
| D$_4$ | human, CHO cells | spiperone (0.2) | haloperidol | 60 min, 27° C. |

The separation of the radioligand that is bound to the receptors from the free radioligand is carried out by filtration through GF/B filters that have been pre-treated with 0.3% polyethyleneimine using a filtration apparatus of the Brandle Cell harvester type. Scintillation liquid is added to the filters, the radioactivity of which is counted using a beta-counter. The IC$_{50}$ (concentration of the compound that inhibits the binding of the radioligand by 50%) is determined by non-linear regression. The K$_i$ is then calculated using the Cheng-Prussof equation: K$_i$=IC$_{50}$/(1+L*/K$_d$) where L* is the concentration of radioligand and K$_d$ is the dissociation constant of the radioligand determined by saturation tests.

The products of the invention have K$_i$ values for the 5HT$_{2A}$ and α$_1$ receptors that are less than $10^{-8}$M. With regard to the D$_2$ selectivity relative to the D$_4$ selectivity; the affinity for the D$_4$ receptor is generally 10 times greater than that for the D$_2$ receptor ($\leq$5 nM for D$_4$ vs.$\geq$50 nM for D$_2$)

In vivo

1. Verticalisation induced by apomorphine (0.75 mg/kg, s.c.) in the mouse

This test, described by Protais et al., Psychopharmacology, 50, 1–6 (1976), allows the evaluation of the dopaminergic antagonist activity of possible antipsychotic products. A mouse to which apomorphine has been administered and which has been placed in a cage with vertical bars will, most of the time, remain immobile at the top of the cage, clinging by its four paws to the bars. This verticalisation behaviour is blocked if a dopaminergic antagonist product has been administered before the apomorphine.

Test immediately after subcutaneous (s.c.) administration of the product or solvent (control group), the mouse is placed in a cylindrical cage (14 cm diam.×14 cm height) with vertical bars. Thirty minutes later, the animal receives the dose of apomorphine (0.75 mg/kg, s.c.). The animals are observed 10 and 20 minutes after the injection of apomorphine and are given one of the following scores each time a measurement is taken: score 0 (four paws on the ground), score 1 (mouse upright, two front paws on the bars) or score 2 (mouse clinging by all four paws to the bars). The verticalisation score used for the results is from 0 to 4 (sum of the two scores). Each experimental group contains at least 5 animals.

Statistical analysis: The effect of the product on verticalisation is evaluated by comparing the scores obtained for each group that has received a dose of product with those obtained for the control group (solvent) using a Mann and Whitney U test with a probability of p<0.05.

The ID$_{50}$ inhibitory dose is that dose of product which reduces by half the average of the verticalisation scores in comparison with the average of the control group.

Results: by way of example, the product of Example 5 has an ID$_{50}$ in this test of 0.22 mg/kg.

2. Active avoidance conditioning in the rat

This test is conventionally used to characterise antipsychotic products, cf. P. A. Janssen, C. J. E. Niemegeers, Arzneim-Forsch., 1037–1043 (1961).

It is carried out in a cage having two compartments with an electrified floor, on rats that have been conditioned in the following manner: on presentation of a light signal, the animal must move from the compartment in which it is situated to the other compartment in order not to receive an electric shock. The response of the animal to the light signal is a conditioned Avoidance response. If the animal does not make that response, at the end of the light signal it receives an electric shock until it goes into the other compartment. The response to the electric shock is an unconditioned Escape response.

Conventionally, anti-psychotic products inhibit the conditioned Avoidance response at doses lower than those which inhibit the non-conditioned Escape response. That differentiates them from other classes of products (in particular, barbiturates and benzodiazepines), which inhibit both responses alike.

Equipment: The equipment consists of a cage divided into 2 compartments by a central partition; an opening in the partition allows the animal to move from one compartment to the other (LE 916 model, LETICA). The floor of each compartment is an electrified grid. The operation of the cage (light signal, passing of the electric current through the grid) and the recording of the movements of the animal from one compartment to the other are carried out by computer (COMPAQ 386S) using the software SHUTTLE 8 (LETICA).

Test: the animals are their own controls. Each daily session comprises 10 tests spaced at intervals of 30 seconds. A test consists of presenting the light signal (10 seconds), followed, or not, by the electric shock (0.460 mA, maximum duration 5 seconds) depending on the response of the animal to the light signal. The effects of a product on the avoidance responses are evaluated during a Test Session which takes places the day after a Control Session during the course of which the animals will have received the solvent. The product or the solvent is administered to the animal 30 minutes before the start of the Session. The parameter used is the number of avoidance responses.

Statistical analysis: For each dose of product the number of avoidance responses obtained in the Test Session is compared with that obtained for the same animals in the Control Session using a Wilcoxon Test with a probability of p<0.05.

The average ID$_{50}$ inhibitory dose is that which reduces the number of conditioned avoidances by 50% compared with the control value.

Results: by way of example, the product of Example 5 administered subcutaneously has an ID$_{50}$ in this test of 0.88 mg/kg.

3. Test of aggressiveness in isolated mice

This test allows the evaluation of the intraspecies anti-aggressive activity of a product in mice that have been kept in isolation for several months.

Animals: The test uses male CD mice (Charles River) weighing from 22 to 25 g on arrival at the animal house. Immediately on arrival the animals are isolated in individual cages made of opaque black polycarbonate (23×14×13 cm) having a grill lid, and are housed for a prolonged period (approximately 6 months) in the experimentation room.

Selection of pairs of mice: The selection of pairs of aggressive mice that will be used on a long-term basis in the study starts after the animals have been isolated for one month. Once or twice per week a mouse from another cage (intruder) is placed in the cage of a (resident) mouse and the two animals are observed to see if they attack one another (sniffing, pursuing, nipping, biting) during that trial. At the end of the trial (maximum duration of 10 minutes), each mouse is isolated again in its own cage. If attacks have occurred, the same pair will be tested again in the next trial; if there have been no attacks, each mouse of that pair will be placed in the presence of a different mouse in the following trial. Thus, in the course of successive trials consisting of 1 or 2 trials per week, definitive pairs of mice that will be used for the experiments are selected. The selection of the pairs is based on the stability of the combative nature of the animals from one trial to the next, the shortness of the latent period before the first attack and the frequency and duration of the attacks. With the pairs selected in that manner, those parameters are checked each week by a quick trial, without treatment, two days before the Test day.

Test: The test takes place once a week. Thirty minutes before the two mice of the pair are placed together, each mouse receives the same treatment (product or solvent) and remains isolated in its respective cage. At T0 minute, the intruder mouse is introduced into the cage of the resident mouse for a period of three minutes. The latent period (in seconds) before the first attack and the number and total duration (in seconds) of the attacks are observed. Any reversal of dominance of one mouse in relation to the other (generally the resident mouse is the dominant mouse) is also noted.

At the end of the test, the intruder mouse is returned to its cage; the animals remain in isolation until the next quick trial and test the following week.

Statistical analysis: The effects of a product on aggressiveness are evaluated by comparing the number and duration of the attacks by the pairs that have received the product (treated groups) with those obtained with the pairs that have received the solvent (control group) by using a variance analysis (ANOVA) followed by a Dunnett's test with a probability of $p<0.05$.

The $ID_{50}$ inhibitory dose of the number or duration of the attacks is that dose of product which reduces by half the average of each of those values compared with the average obtained, respectively, in the control group.

Results: by way of example, the product of Example 5 administered subcutaneously has an $ID_{50}$ in this test of 0.18 mg/kg.

4. Induction of catalepsy in the rat

The prolonged administration of "typical" neuroleptics or anti-psychotics (haloperidol, chlorpromazine) to schizophrenic patients often causes the appearance of undesirable extrapyramidal symptoms (EPS) of the Parkinson's type, especially an immobility phenomenon, cf. Davis et al., "Neuroleptics: Neurochemical, Behavioral, and Clinical Perspectives", Eds. Coyle, J. T. and Enna, S. J. Raven Press, New York (1983). "Atypical" anti-psychotics (clozapine), however, cause few extrapyramidal symptoms.

The acute administration of "typical" anti-psychotics to an animal induces catalepsy, that is to say, the animal stays in a posture, often abnormal, which has been imposed upon it by the person carrying out the experiment cf. Waldmeier P. C. et al; Eur. J. of Pharmacology, 55, 363–373 (1979). The evaluation of the cataleptogenic properties of a product in the rat thus makes it possible to know whether, when administered to humans, the product will or will not risk causing an extrapyramidal-type syndrome.

Test: the animals are placed in individual cages and food is withdrawn the day before the test, but drink is taken as desired. The catalepsy test comprises placing each rear paw of the animal on the front paw of the same side and measuring the time (seconds) during which the animal remains in that "crossed paws" position (maximum 30 seconds). Each animal is subjected to three successive tests (one every two minutes), the animal being removed from its cage and placed on the work surface. The tests are carried out one hour after the subcutaneous injection or oral administration of the product or its solvent. The average value of the three tests represents the duration of the catalepsy (in seconds) for each animal. There are five or six rats per experimental group.

Statistical analysis: The effect of the product on the duration of catalepsy is evaluated by an ANOVA, followed by a Dunnett's test, with a probability of $p<0.05$.

The average $ED_{50}$ effective dose of catalepsy induction is that dose which causes a catalepsy of a duration of 50% compared with the maximum value of 30 seconds (corrected by the value of the solvent control group).

Results: by way of example, the product of Example 5 has an $ED_{50}$ in this test of 34 mg/kg, which compares very favourably with the reference compounds such as haloperidol or risperidone which in this test, administered subcutaneously, have an $ED_{50}$ of 0.15 mg/kg and 1.2 mg/kg, respectively.

We claim:

1. A compound selected from the group consisting of 1,2-Benzisoxazole compounds of formula I

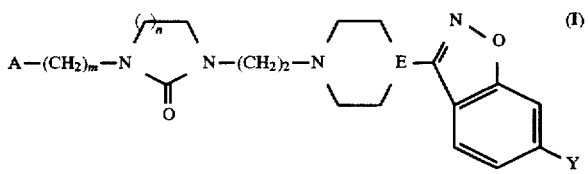

wherein:

A is selected the group consisting of linear and branched alkyl having from 1 to 10 carbon atoms inclusive, unsubstituted phenyl, halophenyl, hydroxyphenyl, and (lower alkoxy)phenyl, m is selected from zero and 1, n is selected from 1 and 2, E is selected from the group consisting of N and CH, and Y is selected the group consisting of hydrogen, halogen, and alkoxy having from 1 to 5 carbon atoms inclusive, optical isomers thereof, and addition salts thereof with a pharmaceutically-acceptable acid.

2. A compound of claim 1 which is 1-{2-[4-(6-fluoro-1,2-benzisoxazol-3-yl)piperazin-1-yl]ethyl}-3-isopropylimidazolidin-2-one.

3. A compound of claim 1 selected from the group consisting of 1-{2-[4-(6-fluoro-1,2-benzisoxazol-3-yl)piperazin-1-yl]ethyl}-3-ethylimidazolidin-2-one and the hydrochloride thereof.

4. A compound of claim 1 which is 1-{2-[4-(6-fluoro-1,2-benzisoxazol-3-yl)piperid-1-yl]ethyl}-3-phenylimidazolidin-2-one.

5. A method for treating a living animal body afflicted with a condition selected from schizophrenia, anxiety, depression, and aggressiveness, comprising the step of administering to the said living animal body an amount of a compound of claim 1 which is effective for alleviation of said condition.

6. A pharmaceutical composition useful for treating schizophrenia, anxiety, depression, or aggressiveness, comprising as active ingredient a compound according to claim 1 together with one or more appropriate pharmaceutical excipients.

* * * * *

UNITED STATES PATENT AND TRADEMARK OFFICE
CERTIFICATE OF CORRECTION

PATENT NO. : 5,780,474
DATED : July 14, 1998
INVENTOR(S) : Jean-Louis Peglion, Mark Millan, Mauricette Brocco, and Valerie Audinot It is certified that error appears in the above-indentified patent and that said Letters Patent is hereby corrected as shown below: On the title page: Item [56]

under References Cited, the first reference; "Strupczewiski et al." should read -- Strupczewski et al. --

Col. 3, line 11; "anxiety or depressive" should read -- anxiety, depressive --.

Col. 7, line 44; "Test immediately" should read -- Test: immediately --.

Col. 10, line 48; Delete "from".

Col. 10, line 55; Delete "from".

Col. 10, line 54, after "selected" should read --from--.

Signed and Sealed this

Fifth Day of January, 1999

Attest:

Attesting Officer

*Acting Commissioner of Patents and Trademarks*